(12) United States Patent
Gencheff

(10) Patent No.: US 9,498,599 B2
(45) Date of Patent: Nov. 22, 2016

(54) METHOD OF CONTROLLABLY DIRECTING A DEVICE INTO A HUMAN VESSEL

(71) Applicant: Frontier Medical Devices, Inc., Marquette, MI (US)

(72) Inventor: Nelson E. Gencheff, Marquette, MI (US)

(73) Assignee: Frontier Medical Devices, Inc., Gwinn, MI (US)

( * ) Notice: Subject to any disclaimer, the term of this patent is extended or adjusted under 35 U.S.C. 154(b) by 136 days.

(21) Appl. No.: 14/531,629

(22) Filed: Nov. 3, 2014

(65) Prior Publication Data

US 2015/0151079 A1 Jun. 4, 2015

Related U.S. Application Data

(63) Continuation-in-part of application No. 14/185,764, filed on Feb. 20, 2014, now abandoned.

(60) Provisional application No. 61/766,809, filed on Feb. 20, 2013.

(51) Int. Cl.
  *A61M 25/01* (2006.01)
  *A61M 25/09* (2006.01)

(52) U.S. Cl.
  CPC ... *A61M 25/0113* (2013.01); *A61B 2090/3966* (2016.02); *A61M 25/0108* (2013.01); *A61M 2210/127* (2013.01)

(58) Field of Classification Search
  CPC ............... A61M 2210/127; A61M 25/0108; A61M 25/0113; A61M 25/0147; A61M 25/09041; A61B 2090/3966
  See application file for complete search history.

(56) References Cited

U.S. PATENT DOCUMENTS

| | | | | |
|---|---|---|---|---|
| 6,093,177 A | * | 7/2000 | Javier, Jr. | A61M 25/0054 604/264 |
| 6,583,689 B2 | * | 6/2003 | Katohno | H03H 9/1014 310/348 |
| 6,673,040 B1 | * | 1/2004 | Samson | A61B 17/12022 604/101.01 |
| 6,695,811 B2 | * | 2/2004 | Samson | A61B 17/12045 604/101.01 |
| 2002/0095175 A1 | * | 7/2002 | Brock | A61B 17/0469 606/205 |
| 2008/0125715 A1 | * | 5/2008 | Cohen | A61M 25/0041 604/164.13 |
| 2010/0030161 A1 | * | 2/2010 | Duffy | A61M 25/0668 604/246 |
| 2010/0331821 A1 | * | 12/2010 | Itou | A61M 25/0041 604/528 |
| 2014/0135786 A1 | * | 5/2014 | Sadanandan | A61M 25/0041 606/108 |

* cited by examiner

*Primary Examiner* — Quynh-Nhu H Vu

(74) *Attorney, Agent, or Firm* — Wood, Phillips, Katz, Clark & Mortimer

(57) ABSTRACT

A method of controllably directing an elongate device into a vessel network including the steps of: obtaining a tubular component with a tubular wall bounding a passageway and having an aperture between spaced ends; directing an introducing member into the vessel network towards a target site; placing the introducing member and tubular component in an operative relationship wherein at least a portion of the introducing member resides within the passageway; relatively repositioning the introducing member and tubular component by guided movement, one against the other, to place the aperture at an introduction location; and directing the device through the passageway to and through the aperture to the target site.

20 Claims, 4 Drawing Sheets

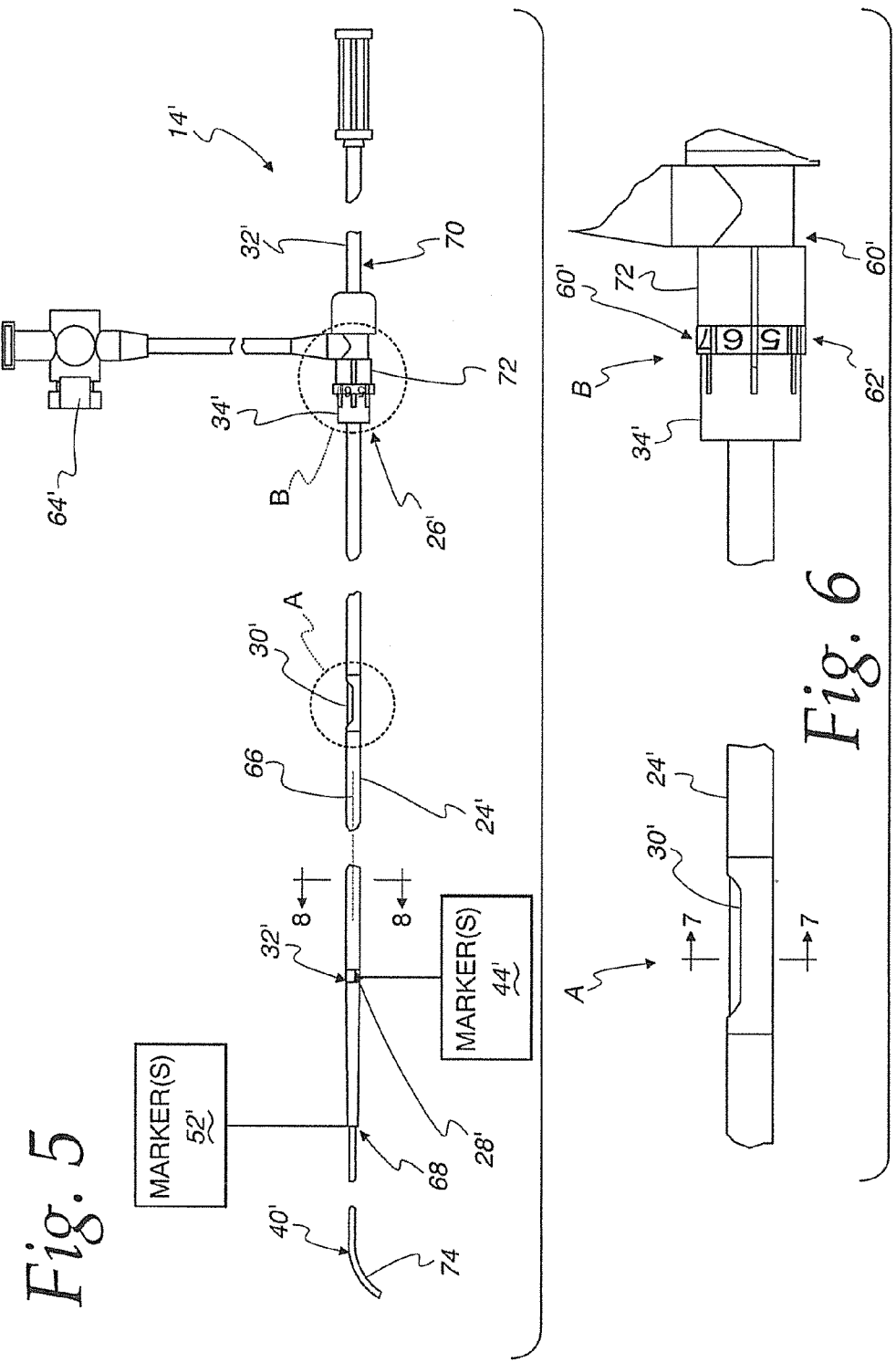

METHOD OF CONTROLLABLY DIRECTING A DEVICE INTO A HUMAN VESSEL

CROSS-REFERENCE TO RELATED APPLICATIONS

This application is a continuation-in-part of U.S. application Ser. No. 14/185,764, filed Feb. 20, 2014.

BACKGROUND OF THE INVENTION

Field of the Invention

This invention relates to surgical procedures and, more particularly, to a method of directing a device into a human vessel, as at the aortic arch.

Background Art

Current catheters are limited by geometry at the aortic arch and by individual patient anatomical variations. Access into the carotid vessels oftentimes requires catheter manipulation in the aorta and in the proximal common carotid vessels. With existing technology, may procedures may require excessive catheter manipulation in the aortic domain. Such catheter manipulations can be cumbersome and endanger the patient because of embolic events, potentially leading to stroke. In situations of unfavorable aortic arch anatomy, contrast volume may be increased, radiation exposure can be excessive, and procedural time may be undesirably prolonged. The procedural risk of stroke and contrast nephropathy may increase while the total radiation exposure to both patient and surgical personnel may multiply. The nature of such procedures is generally such that the surgeon must have a very high level of skill and experience to avoid the potential dangerous outcomes identified above. This is particularly true with unfavorable aortic arch anatomy.

Currently, devices and procedures rely upon the use of "wire rails" to direct a device to a vascular destination in the aortic region. At best, conventional procedures rely upon a relatively unstable platform for the introduced device with success in accessing target vessels often becoming hit or miss based upon a number of variables involved, including experience, anatomical conditions, etc.

SUMMARY OF THE INVENTION

In one form, the invention is directed to a method of controllably directing an elongate device into a vessel network in a human body to access a target site. The method includes the step of obtaining a tubular component having a tubular wall with a length between spaced ends. The tubular wall bounds a passageway and has an aperture between the spaced ends. The method further includes the steps of: obtaining an introducing member; directing the introducing member into the vessel network towards the target site; placing the introducing member and tubular component in an operative relationship wherein at least a portion of the introducing member resides within the passageway; relatively repositioning the introducing member and tubular component by guided movement, one against the other, to place the aperture at an introduction location; and directing the device through the passageway to and through the aperture to the target site.

In one form, the method further includes the steps of obtaining a guide wire and directing the guide wire into the passageway. The step of directing the introducing member into the vessel network involves guiding the introducing member into the vessel network along the guide wire.

In one form, the introducing member has a tubular wall bounding a passageway. The step of guiding the introducing member into the vessel network involves moving the introducing member guidingly against the guide wire with at least a portion of the guide wire within the passageway in the introducing member.

In one form, the introducing member and tubular component are configured so that the introducing member and tubular component can be relatively moved between: a) a first relationship wherein the introducing member blocks the aperture; and b) a second relationship wherein the aperture is either partially or fully opened.

In one form, the step of directing the introducing member into the vessel network involves directing the introducing member into the vessel network with the introducing member and tubular component in the first relationship.

In one form, the step of obtaining a tubular component involves obtaining a tubular component with a marker thereon and further including the step of using a detector to track movement of the marker within the vessel network to thereby track movement of the aperture within the vessel network.

In one form, the marker is at the aperture.

In one form, the step of obtaining an introducing member involves obtaining an introducing member with a marker thereon and further including the step of using a detector to track movement of the marker on the introducing member to thereby track movement of the introducing member within the vessel network.

In one form, the method further includes the steps of changing the introducing member and tubular component from their first relationship into their second relationship after directing the introducing member into the vessel network, and thereafter directing a guide wire through the aperture into a target vessel in the vessel network at the target site.

In one form, the method further includes the step of directing a guide wire into the vessel network. The step of directing the introducing member into the vessel network involves guiding the introducing member along the guide wire with the guide wire at least partially within the passageway and extending into a first vessel within the vessel network.

In one form, the method further includes the steps of drawing an end of the guide wire from the first vessel, directing the end of the guide wire through the aperture into a target vessel in the vessel network, and using the guide wire to direct the device into the target vessel.

In one form, the method further includes the steps of removing the guide wire from the passageway and thereafter directing a guide wire into the passageway and through the aperture into a target vessel in the vessel network and using the guide wire extending into the target vessel to direct the device into the target vessel.

In one form, the first vessel makes up the aortic arch. The target vessel branches from the aortic arch.

In one form, the guide wire in the first vessel has a "U" shape.

In one form, the introducing member and tubular component have lengthwise axes. The method further includes the step of turning the tubular component guidingly relative to the introducing member around the lengthwise axis of the tubular component to controllably situate the aperture to facilitate direction of the device through the aperture to the target site.

In one form, the method further involves the steps of obtaining a calibrated control mechanism with a viewable display at a proximal region of the tubular component and using the calibrated control mechanism to selectively turn the tubular component around its lengthwise axis an amount that is determinable by observing the visual display.

In one form, the target vessel is one of a head and neck vessel.

In one form, the method further includes the step of directing a dye through a valve and into the passageway.

In one form, the guide wire has an end formed into a "J" shape.

In one form, the step of obtaining a tubular component involves obtaining a tubular component with a tubular wall having a first distal portion and a second proximal portion. The first distal portion has the aperture therein and is more flexible than the second proximal portion.

BRIEF DESCRIPTION OF THE DRAWINGS

FIG. 5 is a side elevation view of a modified form of system, according to the invention;

FIG. 6 is an enlarged view of portions of the device in FIG. 5 within the circles A and B;

DETAILED DESCRIPTION OF THE PREFERRED EMBODIMENT

Figure 1:
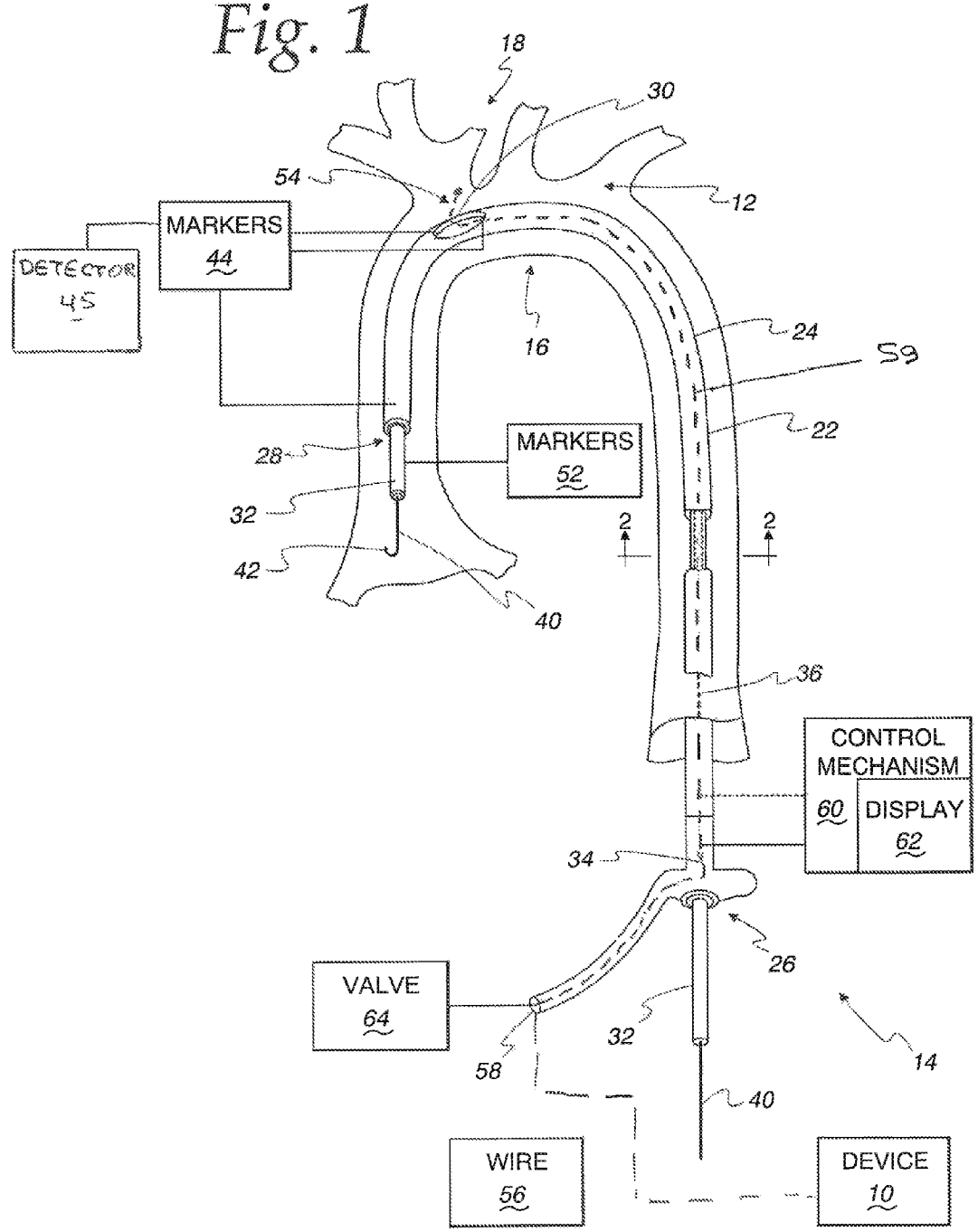
FIG. 1 is a partially schematic representation of a system, according to the present invention, for introducing a device into a human body vessel and including a tubular component with an aperture that is in a vessel at the aortic arch region, preparatory to performing a procedure through a head or neck vessel.
Figure 2:
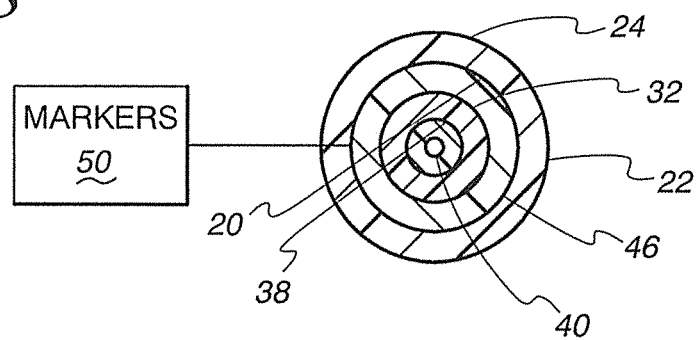
FIG. 2 is an enlarged, cross-sectional view of the system taken along line 2-2 of FIG. 1.

Referring initially to FIGS. 1-4, one form of system for controllably directing a device 10 to a target site in a vessel network 12 in a human body, is shown generally at 14. It should be understood that the system 14 is usable in any human or non-human vessel network, but has particular utility in the region of the aortic arch at 16, wherein the target site is in one or more of the vessels at 18 leading to a patient's head or neck.

Further, the nature of the device 10 is not limited other than by the fact that it is desirably introducible into a passageway 20 bounded by a tubular wall 22 on a tubular component 24. The tubular wall 22 has a length between proximal and distal ends 26, 28, respectively. An elongate aperture 30 is formed through the tubular wall 22 between the ends 26, 28.

The system 14 further includes an introducing member 32. The introducing member 32 and tubular component 24 are placed in an operative relationship with at least a portion of the introducing member 32 residing within the passageway 20.

The tubular component 24 may have different diameters and, in the embodiment shown, has an associated hub 34. The hub 34 facilitates turning of the tubular component 24 around its lengthwise, central axis 36. The hub 34 may be compatible with commercially available devices in the event that other connecting elements may be necessary for a given procedure. The ability to turn the hub 34 and thus the tubular component 24 around its axis 36 facilitates alignment of the aperture 30 with a particular target vessel.

The introducing member 32 has a tubular wall bounding a passageway 38 into which a guide wire 40 extends. The introducing member 32 and guide wire 40 facilitate atraumatic positioning of the tubular component 24 at its aortic arch destination, as shown in FIG. 1.

The introducing member 32 may have a lubricious surface. Alternatively, some form of lubrication may be applied strategically to guide movement of the introducing member 32 relative to the tubular component 24.

The introducing member 32 may be removed from the passageway 20 after the tubular component 24 is placed into the aortic arch. The guide wire 40 may remain within the passageway 20 to be used to access the target vessel/site. In one form, the guide wire 40 is a 0.038 inches wire with a free end 42 formed into a "J" shape.

The distal end 28 of the tubular component 24 has a soft tip that limits trauma to the interior wall of the aorta as the tubular component 24 is advanced through the vessel network 12. Preferably, the distal one-third of the length of the tubular wall 22 is flexible but resistant to kinking or buckling. At least the proximal region is more rigid than the distal one-third of the length of the tubular wall 22.

The tubular component 24 has one or more markers 44 on the surface thereof or embedded therein. The markers 44 may be radio opaque markers that may straddle the aperture 30 or be otherwise strategically placed, as near the distal end 28. Using conventional angiographic assistance technology, the markers 44 can be tracked through an appropriate detector 45 to align the aperture 30 with the particular target vessel 18.

In this embodiment, there is a separate sleeve 46 interposed between the introducing member 32 and the tubular component 24. The sleeve 46 is optional and has multiple functions, including that performed by the introducing member 32. The sleeve 46 will be considered herein to be an "introducing member" which has the additional function of selectively closing and opening the aperture 30. By eliminating the introducing member 32, the sleeve/introducing member 46 might be used in the same manner as described for the introducing member 32.

Figure 3:
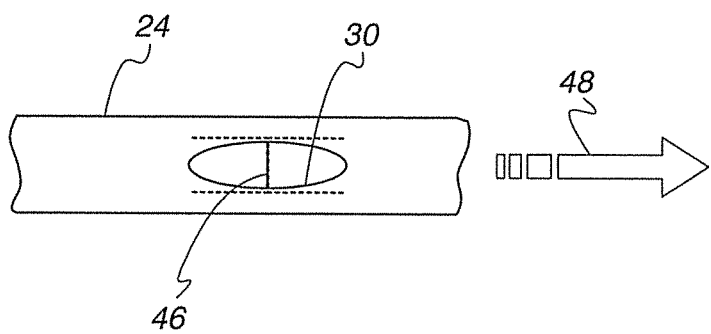
FIG. 3 is an enlarged, fragmentary, elevation view of a length of the tubular component with the aperture therein and with an introducing member situated to partially open the aperture.
Figure 4:
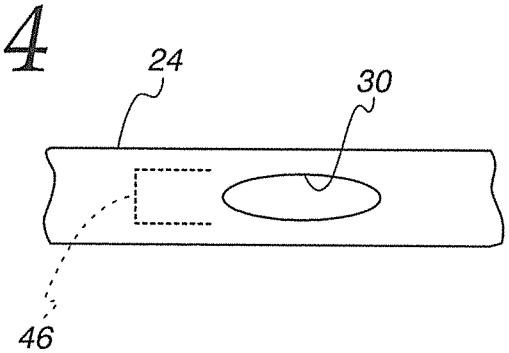
FIG. 4 is a view as in FIG. 3 wherein the introducing member fully blocks the aperture.
Figure 7:
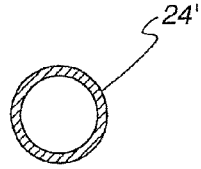
FIG. 7 is a cross-sectional view of a tubular component on the system taken along line 7-7 of FIG. 6.
Figure 8:
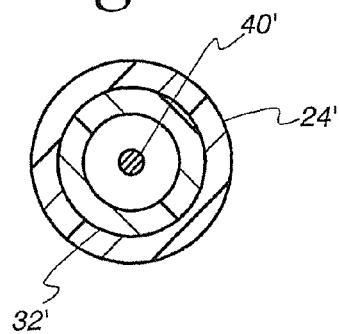
FIG. 8 is an enlarged, cross-sectional view of the system taken along line 8-8 of FIG. 5.

The tubular component 24 and sleeve/introducing member 46 are configured so that the sleeve/introducing member 46 and tubular component 24 can be relatively moved between: a) a first relative relationship, shown in FIG. 4, wherein the sleeve/introducing member 46 blocks the aperture 30; and b) a second relationship, as shown in FIG. 3, wherein the aperture 30 is either partially blocked by the sleeve/introducing member 46, as shown, or fully opened, as would result from sliding the sleeve/introducing member 46 further in the direction of the arrow 48 relative to the tubular component 24.

The sleeve/introducing member 46 may have one or more markers 50 thereon to allow a surgeon to identify the relationship between the sleeve/introducing member 46 and tubular component 24. The markers may be of any known form, such as a radio opaque marker. One or more markers 52 may be provided on the introducing member 32, for the same purpose and may be tracked through an appropriate detector, such as the detector 45.

In a typical procedure, the introducing member 32 is directed into the vessel network 12 towards the target site-in this case one of the vessels 18. With the introducing member 32 and tubular component 24 in an operative relationship, with at least a portion of the introducing member 32 residing within the passageway 20, the tubular component 24 and introducing member 32 are relatively repositioned by advancing the tubular component 24 guidingly against the introducing member 32 so as to ultimately place the aperture 30 at an introduction location at 54 at the entry to one of the vessels 18. The sleeve/introducing member 46 may be maintained in the FIG. 4 relationship as the introducing member 32 is advanced. Once the tubular component 24 is in the FIG. 1 position, the sleeve/introducing member 46 can be retracted from the FIG. 4 position to or past the FIG. 3 position to open the aperture 30.

With the sleeve/introducing member 46 in the FIG. 3 position, or positioned to fully open the aperture 30, the guide wire 40 can be used by being advanced through the aperture 30 into the target vessel 18. Alternatively, if the guide wire 40 is fully withdrawn, together with the introducing member 32, a new wire 56 may be introduced into the passageway 20 and directed up to the target vessel 18 through the aperture 30. Aperture sizing may be selected to permit use of devices to perform, for example, carotid stent procedures, cerebral vascular coiling and acute stroke intervention. Conventional fluoroscopic detector/guidance structure and procedures may be utilized to guide the wire 40, 56 through the aperture 30 to the appropriate target site.

The device 10 may be any type of diagnostic or therapeutic catheter, as used for example in angiography or therapeutic activity. Introduction of the device 10, and other components, may be made through an injection port 58, which may be connected as through a standard manifold, to complete a procedure. The path of the introduced device 10 is identified in FIG. 1 by the dotted line 59, up to the introduction location 54.

By providing a stable platform for better support to access the head and neck vessels at 18, and allowing adaptation to complex geometries, little or no direct catheter manipulation may be required. The inventive design may help avoid guide wire and catheter prolapse, which commonly occurs while accessing the carotid vessels. As a result, overall safety may be improved in performing diagnostic and therapeutic procedures targeting the carotid and cerebral vessels. With the supporting platform, accurate vascular target entry can be effected with potentially an overall reduction of embolic risk, procedure time, radiation exposure, and contrast volume.

The angular orientation between the tubular component 24 and the introducing member 32 can be controlled and identified through a mechanism shown schematically at 60. The control mechanism 60 interacts between the tubular component 22 and introducing member 32 and allows a user to closely control the angular relationship therebetween with respect to their respective lengthwise, central axes. At the same time, a display 62 gives the user a visual indication of this relationship. This allows a more controlled presentation of the aperture 30 at the desired target vessel location, whereupon the device 10 can be precisely guided during a procedure. The control mechanism 60 may have calibration components thereon at the proximal region of the tubular component 24 to facilitate precise, controlled movement of the device 10 in the vicinity of the aortic arch 16.

A valve 64 may be provided to facilitate direction of a dye into the passageway 20 through the injection port 58 or at another location on the system 14.

A modified form of system, according to the invention, is shown at 14' in FIGS. 5-8, wherein components corresponding to those in the system 14 are identified with the same reference numeral with the addition of a "'" designation. In this embodiment, a tubular component 24' has a hub 34' at its proximal end 26' so that the hub 34' and tubular component 24' move as a unit around the lengthwise central axis 66 of the tubular component 24'.

A radio opaque marker 44' is provided at least at the distal end 28' of the tubular component 24'.

A hollow introducing member 32' has at least one marker 52', preferably on at least the distal end 68 thereof. In this embodiment, the introducing member 32' tapers towards the distal end 68. A proximal end 70 of the introducing member 32' has an associated hub portion 72 that cooperates with the hub 34' to allow controlled relative angular positioning between the tubular component 24' and introducing member 32', thereby to allow precision control of the location of the aperture 30'.

The introducing member 32' also functions to provide support and allow atraumatic delivery of the tubular component 24' to its ultimate destination.

The inside and outside of the tubular component 24' may be coated with a lubricious material to limit frictional forces and facilitate vascular delivery. The passageway of the introducing member 32' is sized to accommodate standard guide wires 40', typically less than 0.038 inches in diameter. The guide wire 40' has a bent end at 74.

In both embodiments, the region within which the aperture 30, 30' is formed may be made from radio opaque stainless steel and has a size sufficient to accommodate standard size catheters to complete either imaging or therapeutic procedures in the head and/or neck vessels.

Typically, after the tubular component 24' is formed into the "U" shape conforming around the U-shaped guide wire at the aortic arch, the tubular component 24' will be retracted so that the portion thereof with the aperture 30' resides at the proximal portion of the thoracic aorta. Through the hub 34', the angular position of the aperture 30' can be changed, after which the tubular component 24' can be advanced again closer to the target site. Typically, a 90° turn will be affected.

As seen in FIG. 6, the control mechanism 60', made up of at least the hub 34' and hub portion 72, incorporates a numerical display 62' which allows the user to calibrate and control the orientation of the aperture 30' within the vessel network 12. Thereafter, the introducing member 32' can be removed, or partially backed out to fully or partially open the aperture 30' to permit deployment of diagnostic or therapeutic hardware into the head and neck vessels 18.

In this embodiment, a two-way valve 64' is shown for monitoring and dye delivery.

Figure 9:
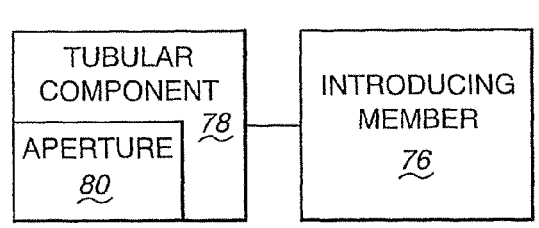
FIG. 9 is a schematic representation of the inventive system, including the specific embodiments in FIGS. 1-8.

As shown in FIG. 9, a generic form of the inventive system 14" is made up of at least one introducing member 76 and a tubular component 78 with an aperture 80. The tubular component 78 encompasses the tubular components 24, 24' and variations thereof, while the introducing member 76 encompasses the introducing members 32, 32', 46 and variations thereof. The generic showing of these components is intended to encompass the specific embodiments herein and variations thereof which would be obvious to one skilled in the art with the inventive teachings in hand.

Figure 10:
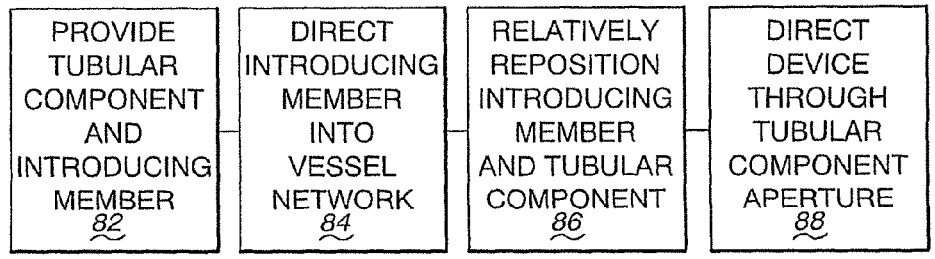
FIG. 10 is a flow diagram representation of a method of controllably directing a device into a vessel network in a human body to access a target site.

With the inventive system 14, 14', 14", a method of controllably directing an elongate device into a vessel network in a human body to access a target site can be carried out as shown in flow diagram form in FIG. 10.

As shown at block 82, a tubular component and introducing member are provided. The tubular component has an aperture.

As shown at block 84, the introducing member is directed into a vessel network.

As shown at block 86, the introducing member and tubular component are relatively repositioned to strategically situate the aperture on the tubular component.

As shown at block 88, a device is directed through the tubular component aperture to perform a diagnostic or therapeutic procedure.

The foregoing disclosure of specific embodiments is intended to be illustrative of the broad concepts comprehended by the invention.

The invention claimed is:

1. A method of controllably directing an elongate device into a vessel network in a human body to access a predetermined target site, the method comprising the steps of:
    obtaining a tubular component comprising a tubular wall with a length between spaced ends, the tubular wall bounding a passageway and having an aperture between and spaced from each of the spaced ends;
    obtaining an introducing member;
    directing the introducing member into the vessel network towards the target site;
    placing the introducing member and the tubular component in an operative relationship wherein at least a portion of the introducing member resides within the passageway;
    relatively repositioning the introducing member and tubular component by guided movement, one against the other, to place the aperture at a predetermined introduction location within the vessel network; and
    directing the elongate device through the passageway to and through the aperture to the target site.

2. The method of controllably directing the elongate device into the vessel network according to claim 1 further comprising the steps of obtaining a guide wire and directing the guide wire into the passageway and wherein the step of directing the introducing member into the vessel network comprises guiding the introducing member into the vessel network along the guide wire.

3. The method of controllably directing the elongate device into the vessel network according to claim 2 wherein the introducing member has a tubular wall bounding a passageway and the step of guiding the introducing member into the vessel network comprises moving the introducing member guidingly against the guide wire with at least a portion of the guide wire within the passageway in the introducing member.

4. The method of controllably directing the elongate device into the vessel network according to claim 1 wherein the introducing member and the tubular component are configured so that the introducing member and the tubular component can be relatively moved between: a) a first relationship wherein the introducing member blocks the aperture; and b) a second relationship wherein the aperture is either partially or fully opened.

5. The method of controllably directing the elongate device into the vessel network according to claim 4 wherein the step of directing the introducing member into the vessel network comprises directing the introducing member into the vessel network with the introducing member and the tubular component in the first relationship.

6. The method of controllably directing the elongate device into the vessel network according to claim 1 wherein the step of obtaining the tubular component comprises obtaining the tubular component with a marker thereon and further comprising the step of using a detector to track movement of the marker within the vessel network to thereby track movement of the aperture within the vessel network.

7. The method of controllably directing the elongate device into the vessel network according to claim 6 wherein the marker is at the aperture.

8. The method of controllably directing the elongate device into the vessel network according to claim 1 wherein the step of obtaining the introducing member comprises obtaining the introducing member with a marker thereon and further comprising the step of using a detector to track movement of the marker on the introducing member to thereby track movement of the introducing member within the vessel network.

9. The method of controllably directing the elongate device into the vessel network according to claim 5 further comprising the steps of changing the introducing member and the tubular component from their first relationship into their second relationship after directing the introducing member into the vessel network and thereafter directing a guide wire through the aperture into a target vessel in the vessel network at the target site.

10. The method of controllably directing the elongate device into the vessel network according to claim 9 further comprising the step of directing a guide wire into the vessel network and the step of directing the introducing member into the vessel network comprises guiding the introducing member along the guide wire with the guide wire at least partially within the passageway and extending into a first vessel within the vessel network.

11. The method of controllably directing the elongate device into a vessel network according to claim 10 further comprising the steps of drawing an end of the guide wire from the first vessel, directing the end of the guide wire through the aperture into a target vessel in the vessel network, and using the guide wire to direct the device into the target vessel.

12. The method of controllably directing the elongate device into the vessel network according to claim 2 further comprising the steps of removing the guide wire from the passageway and thereafter directing the guide wire into the passageway and through the aperture into a target vessel in the vessel network and using the guide wire extending into the target vessel to direct the device into the target vessel.

13. The method of controllably directing the elongate device into the vessel network according to claim 10 wherein the first vessel defines a patient's aortic arch and the target vessel branches from the aortic arch.

14. The method of controllably directing the elongate device into the vessel network according to claim 10 wherein with the guide wire in the first vessel the guide wire has a "U" shape.

15. The method of controllably directing the elongate device into the vessel network according to claim 1 wherein the introducing member and tubular component have lengthwise axes and further comprising the step of turning the tubular component guidingly relative to the introducing member around the lengthwise axis of the tubular component to controllably situate the aperture to facilitate direction of the device through the aperture to the target site.

16. The method of controllably directing the elongate device into the vessel network according to claim 15 further comprising the steps of obtaining a calibrated control mechanism with a viewable display at a proximal region of the tubular component and using the calibrated control mechanism to selectively turn the tubular component around its lengthwise axis an amount that is determinable by observing the visual display.

17. The method of controllably directing the elongate device into the vessel network according to claim 11 wherein the target vessel is one of a head and neck vessel.

18. The method of controllably directing the elongate device into the vessel network according to claim 1 further comprising the step of directing a dye through a valve and into the passageway.

19. The method of controllably directing the elongate device into the vessel network according to claim 2 wherein the guide wire has an end formed into a "J" shape.

20. The method of controllably directing the elongate device into the vessel network according to claim 1 wherein the step of obtaining the tubular component comprises obtaining the tubular component having the tubular wall having a first distal portion and a second proximal portion, the first distal portion having the aperture therein and more flexible than the second proximal portion.

* * * * *